United States Patent [19]

Chen

[11] 4,112,079

[45] Sep. 5, 1978

[54] ISOLATION OF UTEROEVACUANT SUBSTANCES FROM PLANT EXTRACTS

[75] Inventor: Robert H. K. Chen, Belle Mead, N.J.

[73] Assignee: Ortho Pharmaceutical Corporation, Raritan, N.J.

[21] Appl. No.: 822,479

[22] Filed: Aug. 8, 1977

[51] Int. Cl.$^2$ .................. A61K 35/78; A61K 31/335; C07D/301/00; C07G 17/00
[52] U.S. Cl. ................................. 424/195; 424/278; 260/236.5; 260/333; 210/31 C
[58] Field of Search ........................ 260/236.5, 333; 210/31 C; 424/195

[56] References Cited

U.S. PATENT DOCUMENTS

| | | | |
|---|---|---|---|
| 3,986,952 | 10/1976 | Kanojia et al. | 210/31 C |
| 3,996,132 | 12/1976 | Mateos et al. | 210/31 C |
| 4,006,227 | 2/1977 | Gallegos et al. | 424/195 |
| 4,046,882 | 9/1977 | Kanojia | 424/195 |
| 4,060,604 | 11/1977 | Kanojia | 424/195 |

Primary Examiner—Donald B. Moyer
Attorney, Agent, or Firm—Benjamin F. Lambert

[57] ABSTRACT

A method of obtaining uteroevacuant substances from the zoapatle plant is described. The isolation and purification of biologically-active compounds from the zoapatle plant is accomplished by chemical means.

19 Claims, No Drawings

ISOLATION OF UTEROEVACUANT SUBSTANCES FROM PLANT EXTRACTS

In co-pending application Ser. No. 672,918 now U.S. Pat. No. 4,086,358, a method is described for isolating and purifying the active principles in the zoapatle plant. These materials have been shown to posses uteroevacuant properties. In the process described in the above-noted application, a crude extract is first obtained by a series of extraction and purification steps and the crude extract is further purified by chromatography over silicic acid. As a result of the chromatograph, a semi-purified mixture containing at least three major components is obtained. This mixture is then chromatographed through a column of a polymeric gel. A number of fractions are collected and the composition of each fraction is monitored by either gas chromatography or thin layer chromatography. As a result of the second chromatogram, two chemically distinct compounds are obtained as evidenced by gas chromatography and spectral analyses. These compounds have the following formulae.

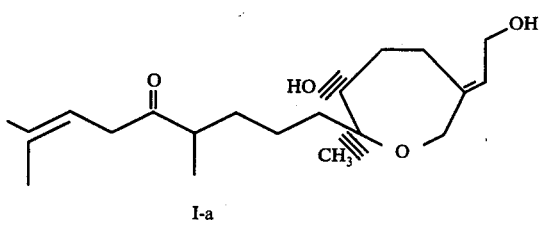

I-a

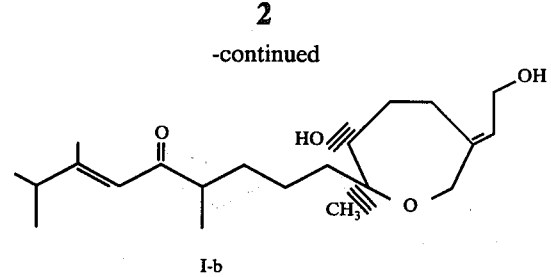

I-b

The present invention relates to a chemical method of isolating, separating and purifying semi-purified mixtures of the zoapatle plant to obtain the biologicallyactive compounds.

The zoapatle plant is a bush about 2 m. high that grows wild in Mexico. Botanically it is known as *Montanoa tomentosa* according to Cervantes, Fam. Compositae, Tribe Helianthae; another variety of the species is *Montanoa floribunda*. The plant is described in great detail in *Las Plantas Medicinales de Mexico*, third edition, Ediciones Botas (1944).

The plant has been used for centuries in the form of a "tea" or other crude aqueous preparations primarily as a labor inducer or menses inducer for humans. Its use as a uteroevacuant agent has been documented in the literature, but definitive chemical and pharmacological studies have not been described. By uteroevacuant is meant an agent which causes the uterus of warm blooded animals to contract or expel its contents. Such agents are generally employed to induce menses, expel a hydatiform mole, expel or resorb a fetus, induce abortion or delayed labor and in situations in which the contents of the uterus, such as the fetus or placenta, should be evacuated.

The process of the present invention is illustrated by the following reaction sequence wherein R is an acyl group derived from an aliphatic acid.

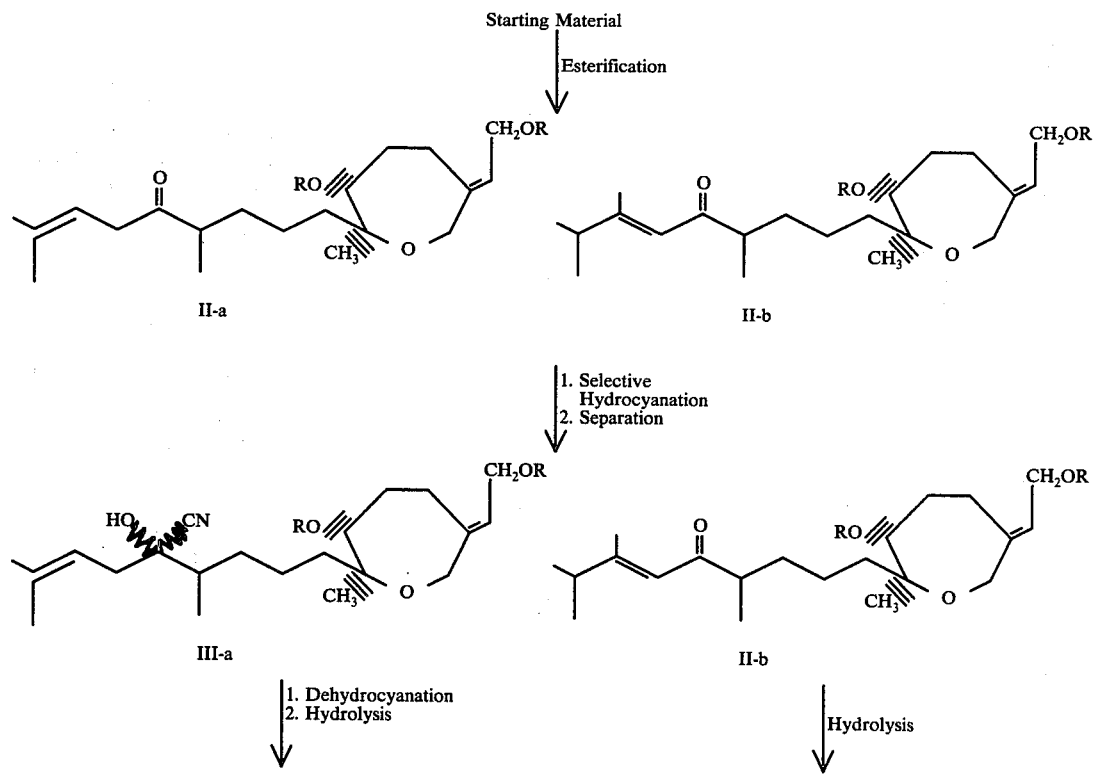

-continued

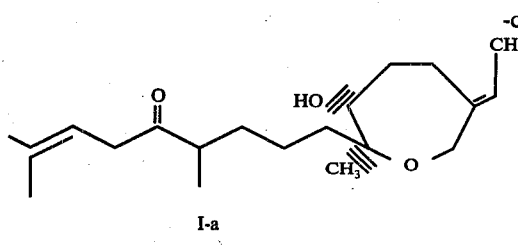

I-a

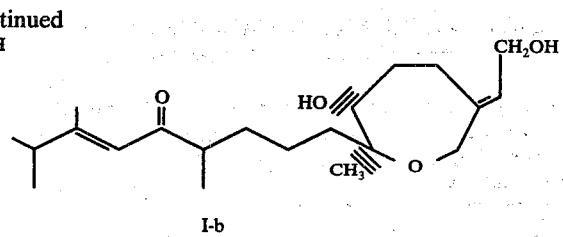

I-b

As the starting material in the process of the present invention, the semi-purified material containing at least three major components obtained as described in Ser. No. 672,918 is employed. The semi-purified residue is first converted to the acyl derivatives by reaction with an excess of an acyl halide or an acid anhydride. The acylation step is preferably carried out in the presence of a base. Acyl halides or acid anhydrides having 1-10 carbon atoms in the acyl group may be employed. The preferred acylating agents are the acetyl, propionyl, butyryl and valeryl halides and the corresponding anhydrides. Bases which may be employed in the acylation step include trialkylamines such as triethylamine, trimethylamine and tripropylamine, and tertiary amines such as pyridine, N,N-dimethylaniline and N,N-diethylaniline. The reaction is preferably carried out in an inert atmosphere such as nitrogen or argon, for example, and at a temperature between about 0°-30° C. The reaction may be carried out in an organic solvent such as, for example, benzene, ether, tetrahydrofuran, toluene and the like. The acylated materials II-a and II-b are obtained from the reaction mixture by techniques known to those skilled in the art. For example, the organic base can be removed by extraction with a dilute aqueous acid solution or an aqueous saturated copper sulfate solution. The crude mixture of acyl derivatives is then obtained by removal of the solvent.

The mixture of the acyl derivatives is converted to a mixture of II-b and III-a by reaction with a selective cyanohydrin forming agent. Suitable agents include a mixture of an alkali metal cyanide such as potassium or sodium cyanide, for example, and a strong mineral acid such as concentrated hydrochloric acid and acetone cyanohydrin and a catalytic amount of an aqueous base such as sodium or potassium carbonate. The reaction is preferably carried out with an excess of the hydrocyanating agent in a closed system such as a sealed tube, for example, at room temperature. As the solvent for the reaction, tetrahydrofuran, ether and dimethoxyethane may be employed. Aqueous media may also be employed. The reaction products are obtained from the reaction mixture by methods known to those skilled in the art. Column chromatography over an adsorbent material such as silica gel, alumina or florisil, for example, may be employed to separate the compounds (II-b and III-a). The mixture can also be separated by other physical means such as, for example, gas chromatography or high pressure liquid chromatography.

The cyanohydrin derivative (III-a) is converted to the diacetate (II-a) by reaction with a decyanohydrating agent such as silver nitrate or mercuric nitrate, for example. The reaction is preferably carried out in an inert atmosphere such as nitrogen or argon, for example, at room temperature. As the solvent for the reaction, solvents such as tetrahydrofuran and dimethoxyethane may be employed. Aqueous solvents may also be employed.

The acylated derivatives II-a to II-b are converted to the underivatized uteroevacuant materials I-a and I-b hydrolysis with a suitable base such as, for example, sodium hydroxide, potassium hydroxide, potassium carbonate or tetra n-butyl ammonium hydroxide preferably in a suitable solvent such as methanol, ethanol, isopropanol, benzene, ether and tetrahydrofuran. Aqueous media may also be employed. The hydrolysis reaction is preferably carried out in an inert atmosphere such as nitrogen or argon, for example. The reaction can be carried out at room temperature or at elevated temperatures such as, for example, the reflux temperature of the solvent employed. The crude products I-a and I-b can be further purified by column chromatography over an adsorbent material such as silica gel, alumina or florisil.

The presence of uteroevacuant materials in the products obtained from the reactions is determined through procedures employed for the detection of uterine contractions and interruption of pregnancy. The compounds are identified by thin layer chromatography and spectral analysis.

The purified compounds are effective in inducing uterine contractions when administered in doses ranging from about 1.0 mg. to about 85 mg./kg. The purified compounds are effective in interrupting pregnancy at dosage levels between about 15 to about 100 mg./kg. The preferred dosage range is from about 20-85 mg./kg. As central nervous system depressants, the compounds are active in doses as low as 3.7 mg./kg. The actual dosage employed will depend upon the species of animal to which the compound is administered. The compounds can be administered in formulations prepared according to acceptable pharmaceutical practices. Suitable formulations include solutions, suspensions and solid dosage forms in pharmaceutically acceptable carriers. They can be administered perorally or intravenously or in any conventional manner in accordance with acceptable pharamaceutical practices.

EXAMPLE 1

A. Preparation of the Diacetate Derivatives II-a and II-b

The semi-purified starting material (1.17 g.) is dissolved in a solution of benzene (30 ml.) and pyridine (10 ml.) and the solution is treated while stirring at 0° C with acetyl chloride (5 ml.) under nitrogen. The reaction mixture is allowed to warm to room temperature and is stirred for 4 hrs. The resulting mixture is treated with ice water (10 ml.) and ether (200 ml.). The organic layer is washed with saturated cupric sulfate solution (3 × 100 ml.) and dried (MgSO$_4$). After removal of the solvent in vacuo, the crude mixture obtained (1.21 g.) is used as such in the next step.

B. Formation of the Cyanohydrin III-a

A portion of the mixture (20 mg.) obtained in A above and potassium cyanide (10 mg.) are dissolved in tetrahydrofuran (4.5 ml.) and water (0.5 ml.) in a capped test tube. Concentrated hydrochloric acid (0.2 ml.) is added to this mixture at 0°. The resulting mixture is stirred for 48 hrs. at room temperature. The test tube is carefully opened and ether (15 ml.) and water (5 ml.) are added to the mixture. The organic layer is separated, dried (MgSO$_4$) and evaporated in vacuo to give an oil. This crude product is purified by chromatography on a SilicAR column (3 g.). A mixture of unreacted II-a and II-b (8 mg.) is eluted with 20:80 ether-petroleum ether and III-a (10 mg.) is eluted with 30:70 ether-petroleum ether.

The spectral characteristics of III-a are as follows:
I.R. (CCl$_4$) μ : 2.8, 4.7 and 5.75

N.M.R. (CDCl$_3$)δ: 5.2 (m, 2H, >C=CH—CH$_2$OAc and

>C=CH—CH$_2$—C(CN)(OH) ); 4.44 (d, J=6Hz, 2H,

>C=CH—CH$_2$—OAc); 4.02 (bs, 2H, >C—O—CH$_2$—C=);

2, 1 (s, 6H, CH$_3$—C(=O)—O—); 1.82 and 1.75
[both s, 6H, (CH$_3$)$_2$—C=CH—] and 1.1 (s, 3H,

>C—O—C(—CH$_3$).

C. Preparation of II-a

A portion of the product (III-a) obtained in B above (2 mg.) is dissolved in tetrahydrofuran (2 ml.) and water (0.2 ml.). To this mixture is added silver nitrate (2 mg.) and the resulting mixture is stirred for 5 mins. at room temperature under nitrogen. Ether (5 ml.) and water (2 ml.) are added to the mixture. The organic layer is separated, dried (MgSO$_4$) and evaporated in vacuo to give II-a as an oil (1.6 mg.).

D. Preparation of I-a

The crude product (II-a) obtained in C above (161 mg.) is dissolved in tetrahydrofuran (5 ml.) and water (5 ml.). To this mixture, tetra n-butyl ammonium hydroxide (20% solution in methanol, 1 ml.) is added under nitrogen at room temperature and the resulting mixture is stirred for 40 hrs. The mixture is treated with 50 ml. of ether and the organic layer is washed with 10% hydrochloric acid (2 × 15 ml.), dried (MgSO$_4$) and evaporated in vacuo to give an oil. This crude product is purified by chromatography on a SilicAR column (5 g.). The compound I-a (81.8 mg.) is eluted with ether. Its ir, nmr spectra, R$_f$ on thin layer and retention time on gas chromatography are identical to those of compound I reported in co-pending application Ser. No. 672,918. The compound has the following spectral characteristics:

I.R. (Neat) μ : 2.91 and 5.88

N.M.R. $\frac{CDCl_3}{TMS}$ δ: 5.41 (m, 2H, >C=CH—CH$_2$OH and

>C=CH—CH$_2$—C(=O)—); 4.20 (d, 2H, >C=CH—CH$_2$OH);

4.15 (s, 2H, >C—O—CH$_2$—C=); 3.58 [broad t, 1H,

>CH(OH)]; 3.18 (d, 2H, >C=CH—CH$_2$—C(=O)—); 1.71

[d, 6H, >C=C—(CH$_3$)$_2$]; 1.15 (s, 3H, >C—O—C(—CH$_3$)

Mass Spec [m/e]: 320 [M-18], 251, 233, 221, 171, 143, 141, 137, 113, 97, 95, 81, 69 Chemical Ionization: M$^+$ + H = 339; M.W. = 338

E. Preparation of I-b

A crude sample of the keto derivative (II-b) (243 mg.) is dissolved in tetrahydrofuran (5 ml.) and water (5 ml.). To this mixture tetra n-butyl ammonium hydroxide (20% solution in methanol, 1.5 ml.) is added under nitrogen at room temperature and the resulting mixture is stirred for 16 hrs. The mixture is treated with 50 ml. of ether and 20 ml. of water. The organic layer is separated, dried (MgSO$_4$) and evaporated in vacuo to give an oil. This crude product is further purified by chromatography on a SilicAR (a neutral silica gel product sold by Mallinckrodt, Inc., St. Louis, Missouri) column (10 g.). The product I-b (152 mg.) is eluted with ether. Its ir, nmr spectra, R$_f$ on thin layer and retention time on gas chromatography are identical to those of compound II, reported in co-pending application Ser. No. 672,918. The compound has the following spectral characteristics:

I.R. (Neat) μ : 2.90, 5.96 and 6.21

N.M.R. $\frac{CDCl_3}{TMS}$ δ: 6.11 (broad s, 1H, —C(=O)—CH=C< );

5.48 (m, 1H, >C=CH—CH$_2$OH); 4.19 (d, 2H,

>C=CH—CH$_2$OH); 4.13 (s, 2H, >C—O—CH$_2$—C=);

3.56 [broad t, 1H, —CH(OH)]; 2.10 (d, 3H,

H$_3$C—C=C< ); 1.13 (s, 3H, >C—O—C(—CH$_3$); 1.07 ]d,

6H, >C=C—CH(CH$_3$)$_2$]

Mass Spec [m/e]: 334 [M-18], 225, 140, 111, 95, 81, 69
U.V. - λ max (EtOH): ~ 239 nm [ε=8500]Chemical Ionization: M$^+$ + H = 353; M.W. = 352

A. PREPARATION OF CRUDE EXTRACT

Ten kg. of dried or fresh leaves from the zoapatle plant (*Montanoa tomentosa*) and 30 gallons of water are added to a 100 gallon steam-jacketed stainless steel tank. The mixture is heated at 90°-100° C. for 2.5 hours with periodic stirring. The hot mixture is filtered through gauze to afford a clear dark tea, about 25 gallons in volume. The solid residue in the tank is washed with 4 gallons of hot water, filtered, and the filtrate combined with the tea obtained above. The combined aqueous extracts are extracted with 30 gallons of ethyl acetate. The mixture is stirred vigorously and allowed to settle. The top frothy layer is siphoned off to break the emulsion, and as much ethyl acetate separated as possible.

Another 20 gallons of ethyl acetate are added to the mixture and the above process repeated. The combined ethyl acetate extracts are evaporated at 50° C. under vacuum. The residue is extracted with three portions of hot (75°-80°) benzene (10 liters total). The benzene extracts are evaporated at 50° C. under vacuum and the residue is washed three times with a total of 8 liters of refluxing hexane. The hexane-washed residue is dissolved in 2 liters of acetone, 10 g. of Nuchar is added, and the mixture is stirred 1 hour at room temperature. The charcoal is removed by filtration, and the filtrate evaporated by distillation at 30° C. under vacuum to afford 69 g. of crude extract.

B. PREPARATION OF SEMI-PURIFIED MATERIALS

The crude residue obtained in A above (50 g.) is dissolved in ether (5 l) and the resulting solution is filtered and washed with saturated sodium bicarbonate solution (500 ml.). The ether is dried over anhydrous sodium sulfate, filtered and concentrated to dryness to afford a light yellow oil (44.6 g.). This oil is then dissolved in chloroform (400 ml.) and the solution added to a column (4 in. × 4 ft.) of 2.5 kg. of neutral silicic acid packed in chloroform. The column is eluted with chloroform, chloroformisopropanol mixtures, and 110 fractions are collected. The fractions are evaporated to dryness in vacuo at a temperature below 40° C. The column is eluted as follows:

| Fraction | Volume/Fraction (ml.) | Eluent |
| --- | --- | --- |
| 1-7 | 650 | $CHCl_3$ |
| 8-30 | 500 | isopropanol:$CHCl_3$ (1:41.7) |
| 31-60 | 500 | isopropanol:$CHCL_3$ (1:33.3) |
| 61-105 | 500 | isopropanol:$CHCl_3$ (1:28.6) |
| 106-110 | 500 | isopropanol:$CHCl_3$ (1:25) |

The composition of the fractions is monitored by thin layer chromatography [silica gel, isopropanolchlorform (1:12.5)] and by gas chromatography – 3% OV17 [methyl silicone – phenyl silicone (1:1)] column using a programmed run (150°-250°). Fractions Nos. 78-84 are combined and the solvent removed in vacuo to afford an oily residue (5.1 g.) which contains at least three major components as indicated by gas chromatography.

A portion of the residue (3.2 g.) is then dissolved in benzene (50 ml.) and the solution added to a column (4 in. × 35 in.) packed with 2 kg. of OR-PVA Merck-O-Gel 2000* prepared in benzene. The column is eluted with benzene and a total of 47 fractions is collected. Thin layer chromatography and gas chromatography are used to monitor the composition of the fractions.

* A vinyl acetate copolymer which swells in organic solvents, produced by E. M. Merck, Inc. and sold under the trademark EM Gel ® Type OR-PVA.

| Fractions | Volume/Fraction (ml.) |
| --- | --- |
| 1-7 | 1000 |
| 8-45 | 300 |
| 46-47 | 1000 |

Fractions 23-33 contain 1.73 g. (54%) of the applied material.

(1) Fractions 24-25 are evaporated to give compound I-b as an oil (0.251 g.).
(2) Fraction 31 is evaporated to give compound I-a as an oil (0.326 g.).

The following general procedure is a standard procedure employed to detect uterine contractions in female animals.

PROCEDURE I

Mature female New Zealand rabbits are anesthetized with sodium pentobarbital and ovariectomized. Following a recovery period of one week, the rabbits are treated with 5 μg./day s.c. of 17β-estradiol for 6 consecutive days, followed by treatment with 1.0 mg./day s.c. of progesterone for 7 consecutive days. The uterus and oviducts of the rabbits are perfused 72 hours after the last dose of progesterone according to the method of Heilman, et al., (Fertil. Steril. 23:221-229) with slight modifications. The oviduct and uterus are perfused at a rate of 53 μl./min. The uterus is perfused with a tube extending 1.0 cm. into the lumen of the uterus from the oviducal end. The uterus is ligated at the utero-tubal junction. Another cannula is inserted 1.0 cm. into the uterus through a small incision in the vagina in order to collect perfusate. The material to be tested is administered i.v. through the jugular vein in a vehicle that contains polyethylene glycol 200, polyethylene glycol 400, ethanol and a phosphate buffer. The cannula is attached to a P23-Dc Stathan transducer which in turn is coupled to a Grass Model 5 polygraph and the uterine contractility measured.

Intravenous administration of the compound obtained from Fraction 31 (I-a) is effective in inducing uterine contractions and relaxing the oviduct in 72-hour progesterone withdrawn rabbits in a dose range of 1.0-4.0 mg./kg. The compound obtained from Fractions 24-25 (I-b) is effective when administered in a dose range of from 25-40 mg./kg.

The following general procedure is a standard procedure employed to detect interruption of pregnancy after implantation has occurred.

PROCEDURE II

Mature, Hartley strain, female guinea pigs are continuously cohabited (monogamously) with males until a vaginal plug (copulation plug) is found in the cage. This time is considered to be day 1 of gestation. Groups of 5-6 females are given test materials intraperitoneally in the vehicle described in Procedure I on day 22 of gestation. The pigs are sacrificed between the 25th and 45th day of gestation and examined for evidence of resorption of abortion.

Intraperitoneal administration of the material obtained from Fraction 31 (I-a) is effective in interrupting pregnancy when administered in a dose range from 25-85 mg./kg.

What is claimed is:

1. The method of purifying residues containing biologically-active materials obtained by extraction of the zoapatle plant which comprises the steps of:
treating the residue with an acylating agent selected from the group consisting of aliphatic acyl halides and aliphatic acid anhydrides having 1-10 carbon atoms in the acyl group in the presence of a base selected from the group consisting of trialkylamines, pyridine, N,N-dimethylanaline and N,N-diethylanaline, reacting the resultant mixture with a hydrocyanating agent selected from the group consisting of an alkali metal cyanide and a strong mineral acid, and acetone cyanohydrin and an alkali metal carbonate, and separating the components of the mixture to yield a first compound having two acyl groups and a keto group and a second compound having two acyl groups and a cyanohydrin group.

2. The process of claim 1 wherein the acylating agent is an acyl halide.

3. The process of claim 2 wherein the acylating agent is acetyl chloride.

4. The process of claim 1 wherein the acylating agent is an acid anhydride.

5. The process of claim 1 wherein the acylating agent is acetic anhydride.

6. The process of claim 1 wherein the base is pyridine.

7. The process of claim 1 wherein the hydrocyanating agent comprises potassium cyanide and hydrochloric acid.

8. The process of claim 1 which additionally comprises treating the compound having two acyl groups and a cyanohydrin grouping with a decyanohydrating agent selected from the group consisting of silver nitrate and mercuric nitrate and reacting the compound formed with a base to form a dihydroxy compound.

9. The process of claim 1 which additionally comprises hydrolyzing the compound having two acyl groups and a keto group with a base selected from the group consisting of alkali metal hydroxides, alkali metal carbonates and tetra n-butyl ammonium hydroxide to form a dihydroxy compound.

10. The process of claim 8 wherein the decyanohydrating agent is silver nitrate and the base is tetra n-butyl ammonium hydroxide.

11. The process of claim 9 wherein the base is tetra n-butyl ammonium hydroxide.

12. The method of purifying residues containing biologically-active materials obtained by extraction of the zoapatle plant which comprises the steps of:

treating the residue with an acylating agent selected from the group consisting of aliphatic acyl halides and aliphatic acid anhydrides having 1-10 carbon atoms in the acyl group in the presence of a base selected from the group consisting of trialkylamines, pyridine, N,N-dimethylanaline and N,N-diethylanaline, reacting the resultant mixture with a hydrocyanating agent selected from the group consisting of an alkali metal cyanide and a strong mineral acid, and acetone cyanohydrin and an alkali metal carbonate, chromatographing the reaction mixture over a column of adsorbent material selected from the group consisting of alumina, florisil and silica gel and collecting multiple fractions to yield a first compound having two acyl groups and a keto group and a second compound having two acyl groups and a cyanohydrin grouping.

13. The process of claim 12 which additionally comprises treating the compound having two acyl groups and a cyanohydrin grouping with a decyanohydrating agent selected from the group consisting of an alkali metal cyanide and a strong mineral acid, and acetone cyanohydrin and an alkali metal carbonate and reacting the compound formed with a base selected from the group consisting of alkali metal hydroxides, alkali metal carbonates and tetra n-butyl ammonium hydroxide to form a dihydroxy compound.

14. The process of claim 12 which additionally comprises hydrolyzing the compound having two acyl groups and a keto group with a base selected from the group consisting of alkali metal hydroxides, alkali metal carbonates and tetra n-butyl ammonium hydroxide to form a dihydroxy compound.

15. The process of claim 12 wherein the adsorbent material is silica gel.

16. The process of claim 12 wherein the acylating agent is acetyl chloride and the hydrocyanating agent comprises potassium cyanide and hydrochloric acid.

17. The process of claim 12 wherein the base is pyridine.

18. The process of claim 14 wherein the base is tetra n-butyl ammonium hydroxide.

19. The process of claim 13 wherein the decyanohydrating agent is silver nitrate and the base is tetra n-butyl ammonium hydroxide.

* * * * *

UNITED STATES PATENT AND TRADEMARK OFFICE
CERTIFICATE OF CORRECTION

PATENT NO. : 4,112,079
DATED : September 5, 1978
INVENTOR(S) : Robert H. K. Chen It is certified that error appears in the above-identified patent and that said Letters Patent are hereby corrected as shown below:

At Column 1, Line 8, "posses" should be -- possess --.
At Column 2, Line 18, "Helianthae" should be -- Heliantheae --.
At Column 4, Line 12, "II-a to II-b" should be -- II-a and II-b --.
At Column 4, Lines 13-14, "materials I-a and I-b hydrolysis" should be -- materials I-a and I-b by hydrolysis --.
At Column 7, Line 17, "(5 1)" should be -- (5 l.) --.
At Column 8, Lines 61-62, "trialkylamines" should be hyphenated as follows -- trialkyl-amines --.
At Column 9, Lines 40-42, "trialkylamines" should be hyphenated as follows -- trialkyl-amines --.

No underscoring whatsoever has been done in the spectral characteristics and they should appear as follows:

At Column 5, Lines 15-17, " $>$C=CH-CH$_2$OAc and" should be
-- $>$C=CH-CH$_2$OAc and --.

At Column 5, Lines 18-20, " $>$C=CH-CH$_2$-C$<$CN, OH )" should be
-- $>$C=CH-CH$_2$-C$<$CN, OH ) --.

At Column 5, Lines 21-23, " $>$C=CH-CH$_2$-OAc); 4.02(bs, 2H, $>$C-O-CH$_2$-C≡ );" should be
-- $>$C=CH-CH$_2$-OAc); 4.02 (bs, 2H, $>$C-O-CH$_2$-C=); --.

UNITED STATES PATENT AND TRADEMARK OFFICE
CERTIFICATE OF CORRECTION

PATENT NO. : 4,112,079
DATED : September 5, 1978
INVENTOR(S) : Robert H. K. Chen It is certified that error appears in the above-identified patent and that said Letters Patent are hereby corrected as shown below:

At Column 5, Lines 23-25, " 2, 1(s,6H,$CH_3$-C(=O)-O-);" should be -- 2, 1 (s, 6H, $C\underline{H}_3$-C(=O)-O-); --.

At Column 5, Lines 26-27, "[both s, 6H, $(CH_3)_2$-" should be -- [both s, 6H, $(C\underline{H}_3)_2$- --.

At Column 5, Lines 28-30, " >C-O-C(-CH$_3$)." should be -- >C-O-C(-$C\underline{H}_3$). --.

At Column 5, Lines 61-62, " >C=CH-$CH_2$OH and" should be -- >C=$C\underline{H}$-$CH_2$OH and --.

At Column 5, Lines 63-65, " >C=CH-$CH_2$-C(=O)-); 4.20(d, 2H, >C=CH-$CH_2$OH);" should be -- >C=$C\underline{H}$-$CH_2$-C(=O)-); 4.20 (d, 2H, >C=CH-$C\underline{H}_2$OH); --.

UNITED STATES PATENT AND TRADEMARK OFFICE
CERTIFICATE OF CORRECTION

PATENT NO. : 4,112,079  Page 3 of 5
DATED : September 5, 1978
INVENTOR(S) : Robert H. K. Chen It is certified that error appears in the above-identified patent and that said Letters Patent are hereby corrected as shown below:

At Column 5, Lines 67-68, " $\rangle$C-O-CH$_2$-C=);" should be

-- $\rangle$C-O-C$\underline{H}_2$-C=); --.

At Column 6, Lines 2-4, " $\rangle$CH(OH)]; 3.18(d,2H, $\rangle$C=CH-CH$_2$-C-);"

should be -- $\rangle$C$\underline{H}$(OH)]; 3.18 (d, 2H, $\rangle$C=CH-C$\underline{H}_2$-C-); --.

At Column 6, Lines 6-8, "[d,6H, $\rangle$C=C-(CH$_3$)$_2$]; 1.15(s, 3H, $\rangle$C-O-C-CH$_3$)"

should be --[d, 6H, $\rangle$C=C-(C$\underline{H}_3$)$_2$]; 1.15(s, 3H, $\rangle$C-O-C-C$\underline{H}_3$) --.

At Column 6, Lines 34-36, "(broad s, 1H, -C-CH=C$\langle$ );" should be

-- (broad s, 1H, -C-C$\underline{H}$=C$\langle$ ); --.

At Column 6, Lines 37-38, " $\rangle$C=CH-CH$_2$OH);" should be

-- $\rangle$C=C$\underline{H}$-CH$_2$OH); --.

UNITED STATES PATENT AND TRADEMARK OFFICE
CERTIFICATE OF CORRECTION

Page 4 of 5

PATENT NO. : 4,112,079
DATED : September 5, 1978
INVENTOR(S) : Robert H. K. Chen It is certified that error appears in the above-identified patent and that said Letters Patent are hereby corrected as shown below:

At Column 6, Lines 40-41, " $>C=CH-CH_2OH$); 4.13 (s, 2H, $>C-O-CH_2-\overset{|}{C}=$);" should be -- $>C=CH-\underline{CH}_2OH$); 4.13 (s, 2H, $>C-O-\underline{CH}_2-\overset{|}{C}=$); --.

At Column 6, Lines 42-43, " $-\overset{|}{C}H(OH)$];" should be -- $-\underline{C}\overset{|}{H}(OH)$]; --.

At Column 6, Lines 45-46, "$H_3C-\overset{|}{C}=C<$); 1.13 (s, 3H, $>C-O-\overset{|}{\underset{|}{C}}-CH_3$);" should be -- $\underline{H}_3C-\overset{|}{C}=C<$); 1.13 (s, 3H, $>C-O-\overset{|}{\underset{|}{C}}-\underline{CH}_3$); --.

At Column 6, Lines 48-49, " $>C=\overset{|}{C}-CH(CH_3)_2$]" should be

UNITED STATES PATENT AND TRADEMARK OFFICE
CERTIFICATE OF CORRECTION

PATENT NO. : 4,112,079

DATED : September 5, 1978

INVENTOR(S) : Robert H. K. Chen

It is certified that error appears in the above–identified patent and that said Letters Patent are hereby corrected as shown below:

$$-- \ge C=\overset{|}{C}-CH(C\underline{H}_3)_2] --.$$

Signed and Sealed this

Thirty-first Day of July 1979

[SEAL]

Attest:

Attesting Officer

LUTRELLE F. PARKER
Acting Commissioner of Patents and Trademarks